(12) United States Patent
Grudic et al.

(10) Patent No.: US 8,512,260 B2
(45) Date of Patent: Aug. 20, 2013

(54) STATISTICAL, NONINVASIVE MEASUREMENT OF INTRACRANIAL PRESSURE

(75) Inventors: Gregory Zlatko Grudic, Longmont, CO (US); Steven Lee Moulton, Littleton, CO (US); Isobe Jane Mulligan, Niwot, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 0 days.

(21) Appl. No.: 13/028,140

(22) Filed: Feb. 15, 2011

(65) Prior Publication Data

US 2011/0201962 A1    Aug. 18, 2011

Related U.S. Application Data

(63) Continuation-in-part of application No. PCT/US2009/062119, filed on Oct. 26, 2009.

(60) Provisional application No. 61/305,110, filed on Feb. 16, 2010, provisional application No. 61/252,978, filed on Oct. 19, 2009, provisional application No. 61/166,499, filed on Apr. 3, 2009, provisional application No. 61/166,486, filed on Apr. 3, 2009, provisional application No. 61/166,472, filed on Apr. 3, 2009, provisional application No. 61/109,490, filed on Oct. 29, 2008.

(51) Int. Cl.
    *A61B 5/03* (2006.01)

(52) U.S. Cl.
    USPC ........... 600/561; 600/300; 600/301; 600/322; 600/323

(58) Field of Classification Search
    USPC .......................... 600/300, 301, 322, 323, 561
    See application file for complete search history.

(56) References Cited

U.S. PATENT DOCUMENTS 5,074,310 A    12/1991    Mick
5,853,364 A    12/1998    Baker, Jr. et al.
(Continued)

FOREIGN PATENT DOCUMENTS

| WO | WO 2007/098957 A1 | 9/2007 |
| WO | WO 2007/149533 A2 | 12/2007 |
| WO | WO 2010/009735 A2 | 1/2010 |
| WO | WO 2010/053743 A1 | 5/2010 |

OTHER PUBLICATIONS

U.S. Appl. No. 13/041,006, filed Mar. 4, 2011 by Grudic et al. and entitled "Active Physical Perturbations to Enhance Intelligent Medical Monitoring."

(Continued)

*Primary Examiner* — Sean Dougherty
(74) *Attorney, Agent, or Firm* — Swanson & Bratschun, L.L.C.

(57) ABSTRACT

Tools and techniques for the rapid, continuous, invasive and/or noninvasive measurement, estimation, and/or prediction of a patient's intracranial pressure. In an aspect, some tools and techniques can predict the onset of conditions such as herniation and/or can recommend (and, in some cases, administer) a therapeutic treatment for the patient's condition. In another aspect, some techniques employ high speed software technology that enables active, long term learning from extremely large, continually changing datasets. In some cases, this technology utilizes feature extraction, state-of-the-art machine learning and/or statistical methods to autonomously build and apply relevant models in real-time.

61 Claims, 6 Drawing Sheets

(56) References Cited

U.S. PATENT DOCUMENTS

| | | | |
|---|---|---|---|
| 5,865,168 A | 2/1999 | Isaza | |
| 6,083,172 A | 7/2000 | Baker, Jr. et al. | |
| 6,094,592 A | 7/2000 | Yorkey et al. | |
| 6,206,830 B1 | 3/2001 | Diab et al. | |
| 6,338,713 B1 | 1/2002 | Chamoun et al. | |
| 6,371,921 B1 | 4/2002 | Caro et al. | |
| 6,409,675 B1 | 6/2002 | Turcott | |
| 6,411,833 B1 | 6/2002 | Baker, Jr. et al. | |
| 6,553,991 B1 | 4/2003 | Isaza | |
| 6,557,553 B1 | 5/2003 | Borrello | |
| 6,558,336 B2 * | 5/2003 | Collins | 600/561 |
| 6,589,189 B2 | 7/2003 | Meyerson et al. | |
| 6,591,122 B2 | 7/2003 | Schmitt | |
| 6,606,509 B2 | 8/2003 | Schmitt | |
| 6,675,031 B1 | 1/2004 | Porges et al. | |
| 6,721,584 B2 | 4/2004 | Baker, Jr. et al. | |
| 6,739,337 B2 | 5/2004 | Isaza | |
| 6,852,083 B2 | 2/2005 | Caro et al. | |
| 7,160,250 B2 * | 1/2007 | Lemaire | 600/301 |
| 7,231,245 B2 | 6/2007 | Greenwald et al. | |
| 7,285,100 B2 * | 10/2007 | Lemaire | 600/561 |
| 7,455,643 B1 | 11/2008 | Li et al. | |
| 7,496,393 B2 | 2/2009 | Diab et al. | |
| 7,547,283 B2 | 6/2009 | Mourad et al. | |
| 7,647,185 B2 | 1/2010 | Tarassenko et al. | |
| 7,654,964 B1 | 2/2010 | Kroll et al. | |
| 7,668,579 B2 | 2/2010 | Lynn | |
| 7,678,057 B2 | 3/2010 | Berkow et al. | |
| 7,720,516 B2 | 5/2010 | Chin et al. | |
| 7,865,224 B2 | 1/2011 | Baker, Jr. et al. | |
| 7,873,497 B2 | 1/2011 | Weber et al. | |
| 7,931,559 B2 | 4/2011 | Phillips et al. | |
| 7,957,780 B2 | 6/2011 | Lamego et al. | |
| 7,976,472 B2 | 7/2011 | Kiani | |
| 8,019,400 B2 | 9/2011 | Diab et al. | |
| 2001/0027335 A1 * | 10/2001 | Meyerson et al. | 607/116 |
| 2003/0060690 A1 | 3/2003 | Jelliffe et al. | |
| 2003/0125612 A1 | 7/2003 | Fox et al. | |
| 2003/0130570 A1 | 7/2003 | Krivitski et al. | |
| 2003/0176931 A1 | 9/2003 | Pednault et al. | |
| 2003/0200189 A1 | 10/2003 | Meng et al. | |
| 2003/0212678 A1 | 11/2003 | Bloom et al. | |
| 2005/0015009 A1 * | 1/2005 | Mourad et al. | 600/438 |
| 2006/0161403 A1 | 7/2006 | Jiang et al. | |
| 2006/0178585 A1 | 8/2006 | Sharrock | |
| 2006/0253016 A1 | 11/2006 | Baker, Jr. et al. | |
| 2007/0015972 A1 | 1/2007 | Wang et al. | |
| 2007/0032732 A1 | 2/2007 | Shelley et al. | |
| 2007/0213619 A1 | 9/2007 | Linder | |
| 2008/0077023 A1 * | 3/2008 | Campbell et al. | 600/502 |
| 2008/0133434 A1 | 6/2008 | Asar et al. | |
| 2008/0154814 A1 | 6/2008 | Chaudhury et al. | |
| 2009/0036754 A1 * | 2/2009 | Pons et al. | 600/301 |
| 2009/0143656 A1 * | 6/2009 | Manwaring et al. | 600/324 |
| 2009/0149751 A1 * | 6/2009 | Mourad et al. | 600/438 |
| 2009/0264776 A1 | 10/2009 | Vardy | |
| 2009/0287105 A1 | 11/2009 | Hirsch | |
| 2009/0292198 A1 | 11/2009 | Kleiven et al. | |
| 2010/0016739 A1 | 1/2010 | Shelley et al. | |
| 2010/0041962 A1 * | 2/2010 | Causevic et al. | 600/301 |
| 2010/0191128 A1 | 7/2010 | Shelley et al. | |
| 2010/0204589 A1 * | 8/2010 | Swoboda et al. | 600/485 |
| 2011/0112799 A1 | 5/2011 | Weber et al. | |
| 2011/0152651 A1 | 6/2011 | Berkow | |
| 2011/0160549 A1 * | 6/2011 | Saroka et al. | 600/301 |
| 2011/0237914 A1 | 9/2011 | Lamego et al. | |

OTHER PUBLICATIONS

U.S. Appl. No. 13/126,727, filed Apr. 28, 2011 by Grudic et al. and entitled "Long Term Active Learning from Large Continually Changing Data Sets."

International Search Report and Written Opinion prepared by the U.S. Patent and Trademark Office as International Searching Authority for PCT International Patent Application No. PCT/US2011/24938, mailed Jun. 7, 2011, 13 pages.

International Search Report and Written Opinion prepared by the U.S. Patent and Trademark Office as International Searching Authority for PCT International Patent Application No. PCT/US2011/027237, mailed May 27, 2011, 16 pages.

International Preliminary Report on Patentability prepared by the International Bureau for PCT/US2009/062119, mailed Feb. 3, 2010, 6 pages.

Berkow (Aug. 2010) Intelomed, Inc., "CVInsight," 14 pages.

Berkow (Jan. 2012) Intelomed, Inc. 510(K) Summary, "CVInsight," 9 pages.

International Search Report and Written Opinion prepared by the U.S. Patent and Trademark Office as International Searching Authority for PCT International Patent Application No. PCT/US12/47659, mailed Oct. 12, 2012, 16 pages.

Shoemaker, et al (2001) CHEST, 120(2):528-537, "Outcome Prediction of Emergency Patients by Noninvasive Hemodynamic Monitoring".

Procopio et al (2008) Intelligent Robots and Systems IEEE/RSJ International Conference, pp. 620-627, "Learning in 1-14 dynamic environments with Ensemble Selection for autonomous outdoor robot navigation".

European Search Report, Jun. 15, 2012 for EP 09825222.4, 10 pages.

International Preliminary Report on Patentability prepared by the International Bureau for PCT/US11/24938), mailed Aug. 30, 2012, 7 pages.

International Preliminary Report on Patentability prepared by the International Bureau for PCT/US11/27237, mailed Sep. 13, 2012, 10 pages.

U.S. Appl. No. 13/554,483, filed Jul. 20, 2012 by Grudic et al. and entitled "Hemodynamic Reserve Monitor and Hemodialysis Control," 57 pages.

* cited by examiner

STATISTICAL, NONINVASIVE MEASUREMENT OF INTRACRANIAL PRESSURE

CROSS-REFERENCE TO RELATED APPLICATIONS

The present disclosure may be related to the following commonly assigned applications/patents:

This non-provisional application claims the benefit, under 35 U.S.C. §119(e), of provisional U.S. Patent Application No. 61/305,110, filed Feb. 16, 2010, by Moulton et al. and titled "A Statistical, Noninvasive Method for Measuring Intracranial Pressure," which is hereby incorporated by reference, as if set forth in full in this document, for all purposes.

This application is also a continuation-in-part of Application No. PCT/US2009/062119, filed Oct. 26, 2009 by Grudic et al. and entitled "Long Term Active Learning from Large Continually Changing Data Sets" (the "'119 Application"), which is hereby incorporated by reference, as if set forth in full in this document, for all purposes. The '119 Application claims the benefit, under 35 U.S.C. §119(e), of provisional U.S. Patent Application Nos. 61/109,490, 61/166,472, 61/166,486, 61/166,499, and 61/252,978, each of which is hereby incorporated by reference, as if set forth in full in this document, for all purposes.

The respective disclosures of these applications/patents are incorporated herein by reference in their entirety for all purposes.

STATEMENT AS TO RIGHTS TO INVENTIONS MADE UNDER FEDERALLY SPONSORED RESEARCH OR DEVELOPMENT

This invention was made with government support under grant number 0535269 awarded by the National Science Foundation; grant number FA8650-07-C-7702 awarded by the Air Force Research Laboratory; and grant numbers W81XWH-09-C-0160 and W81XWH-09-1-0750 awarded by Army Medical Research Material and Command. The government has certain rights in the invention.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

FIELD

The present disclosure relates, in general, tools and techniques for measuring and/or inferring intracranial pressure and more particularly, to solutions that measure and/or infer intracranial pressure noninvasively and/or computationally.

BACKGROUND

Traumatic brain injury ("TBI") is a common and devastating condition. Of the 1.4 million civilians who sustain a TBI each year in the United States, approximately 1.1 million are treated and released from an emergency department, 235,000 are hospitalized, and 50,000 die. Traumatic brain injury is the number one cause of pediatric death and disability. Long-term disability can range from functional changes affecting thinking, language and learning, to physical, emotional and behavioral changes. Traumatic brain injury can cause epilepsy and increase the risk for conditions such as Alzheimer's disease, Parkinson's disease, and other brain disorders that become more prevalent with age.

Traumatic brain injury (TBI) results in an increase in intracranial pressure ("ICP"). Elevated ICP reduces cerebral perfusion pressure ("CPP"), which lowers cerebral blood flow ("CBF"). As the injured brain becomes increasingly more ischemic, brain swelling ensues, causing more ischemia, further brain injury, herniation and oftentimes death. TBI outcome depends on the severity of primary brain injury and the effectiveness of preventing or limiting secondary brain injury.

Evidence-based guidelines for the management of severe traumatic brain injury have been developed, yet a wide spectrum of methods still characterizes most monitoring and treatment strategies. The most widely used, current method for intracranial pressure monitoring involves placement of an intracranial pressure monitoring device. This is an invasive procedure that involves cutting the scalp and drilling a hole through the patient's cranium, so that a pressure transducer can be inserted in or on top of the brain. Newer, non-invasive methods for intracranial pressure and cerebral perfusion monitoring have been described; however, these methods are still considered experimental and none are in clinical practice. These non-invasive, intracranial pressure monitoring methods include: transcranial Doppler ultrasonography; transcranial optical radiation, such as near-infrared spectroscopy; ophthalmodynamometry; arterial pulse phase lag; and ocular coherence tomography.

Further, existing techniques for measuring ICP often will not provide sufficient findings to inform the selection of an appropriate therapeutic strategy for the TBI. Fluid resuscitation strategies are poorly understood, difficult to study and variably practiced. Inadequate resuscitation poses the risk of hypotension and end organ damage. Conversely, aggressive fluid resuscitation may dislodge clots from vascular injuries, resulting in further blood loss, hemodilution and death. How to best proceed when one is dealing with a multiply-injured patient who has a traumatic brain injury and exsanguinating hemorrhage can be especially difficult. Under resuscitation can harm the already injured brain, whereas overresuscitation can reinitiate intracranial bleeding and exacerbate brain swelling, leading to brain herniation, permanent neurological injury and oftentimes death.

Accordingly, new techniques for non-invasive assessment, monitoring, and treatment of TBI, and elevated ICP generally, are urgently needed.

BRIEF SUMMARY

A set of embodiments provides rapid, continuous, invasive, and/or noninvasive techniques for measuring, estimating, and/or predicting a patient's intracranial pressure. In an aspect, certain embodiments can predict the onset of conditions such as herniation and/or can recommend (and, in some cases, administer) a therapeutic treatment for the patient's condition. In another aspect, some embodiments employ high speed software technology that enables active, long term learning from extremely large, continually changing datasets. In some cases, this technology utilizes feature extraction, state-of-the-art machine learning and/or statistical methods to autonomously build and apply relevant models in real-time.

The tools provided by various embodiments include, without limitation, methods, systems, and/or software products.

Merely by way of example, a method might comprise one or more procedures, any or all of which are executed by a computer system. Correspondingly, an embodiment might provide a computer system configured with instructions to perform one or more procedures in accordance with methods provided by various other embodiments. Similarly, a computer program might comprise a set of instructions that are executable by a computer system (and/or a processor therein) to perform such operations. In many cases, such software programs are encoded on physical, tangible and/or non-transitory computer readable media (such as, to name but a few examples, optical media, magnetic media, and/or the like).

Merely by way of example, one set of embodiments provides a computational method of predicting intracranial pressure. In some embodiments, the method comprises receiving, at a computer system, a set of input data from one or more physiological sensors; in an aspect, the input data might pertain to one or more physiological parameters of a patient. The method, in some cases, can further include analyzing, with the computer system, the input data against a pre-existing model to generate diagnostic data concerning the patient's intracranial pressure. The method, then might further comprise displaying, with a display device, at least a portion of the diagnostic data concerning the patient's intracranial pressure.

In a particular embodiment, the diagnostic data comprises an estimate of a current intracranial pressure of the patient, a predicted future intracranial pressure, and/or an estimated pressure at which the patient will suffer a condition, such as uncal herniation. In another embodiment, the input data might comprise periodic samples of a set of continuous, physiological waveform data, such as blood pressure waveform data, to name one example. In accordance with different methods, a variety of sensors may be employed to obtain the input data. Examples include, but are not limited to, an electrocardiograph sensor, an impedance cardiograph sensor, a pulse oximeter, a near infrared sensor, and/or a transcranial Doppler sensor.

In some cases, the method further comprises generating the model to which the input data is applied. In an exemplary embodiment, for example, generating the model might comprise receiving data pertaining to a plurality physiological parameters of a test subject to obtain a plurality of physiological data sets, directly measuring the test subject's intracranial pressure with a reference sensor to obtain a plurality of intracranial pressure measurements, and/or correlating the received data with the measured intracranial pressure of the test subject. This correlation might involve autonomously learning a set of probabilistic predictive models comprises using a linear model framework to identify predictive variables for each increment of data. In other cases, the method might include updating the existing model using the set of input data itself.

Another set of embodiments provides an apparatus. An exemplary apparatus might comprise a non-transitory computer readable medium having encoded thereon a set of instructions executable by one or more computers to perform one or more operations. The set of instructions might, for example, include instructions for receiving a set of input data from one or more physiological sensors, the input pertaining to one or more physiological parameters of a patient, instructions for analyzing the input data against a pre-existing model to generate diagnostic data concerning the patient's intracranial pressure, and/or instructions for displaying, with a display device, at least a portion of the diagnostic data concerning the patient's intracranial pressure.

Yet another set of embodiments provides patient monitoring systems and/or computer systems. An exemplary system might comprise one or more processors; and/ or a computer readable medium in communication with the one or more processors. The computer readable medium, in an aspect, can have encoded thereon a set of instructions executable by the computer system to perform one or more operations, such as the set of instructions described above. The system might include one or more sensors, and/or a therapeutic device.

BRIEF DESCRIPTION OF THE DRAWINGS

A further understanding of the nature and advantages of particular embodiments may be realized by reference to the remaining portions of the specification and the drawings, in which like reference numerals are used to refer to similar components. In some instances, a sub-label is associated with a reference numeral to denote one of multiple similar components. When reference is made to a reference numeral without specification to an existing sub-label, it is intended to refer to all such multiple similar components.

DETAILED DESCRIPTION OF CERTAIN EMBODIMENTS

Figure 1:
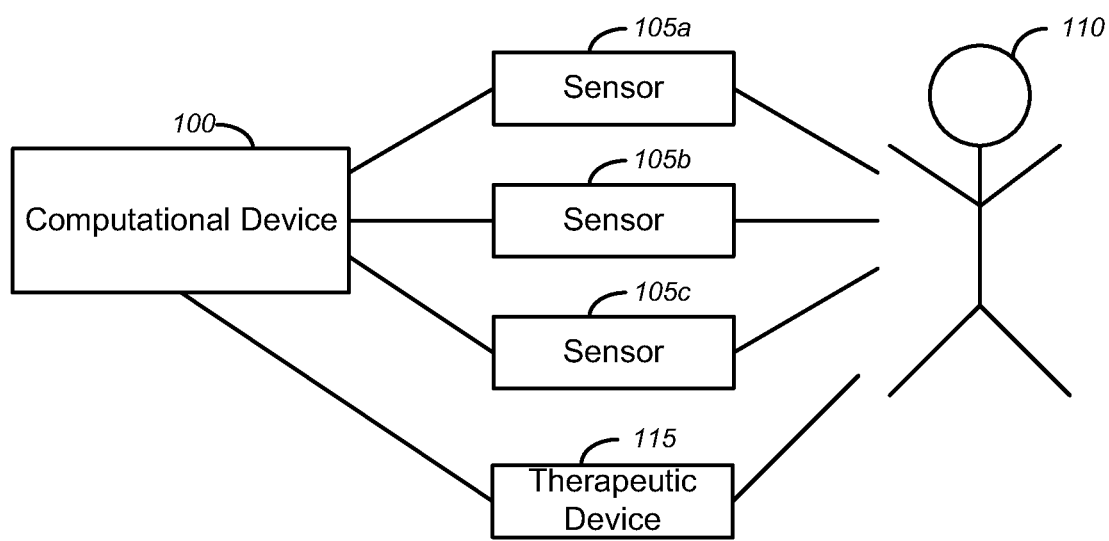
FIG. 1 is a schematic diagram illustrating a basic structure for various embodiments.

While various aspects and features of certain embodiments have been summarized above, the following detailed description illustrates a few exemplary embodiments in further detail to enable one of skill in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present may be practiced without some of these specific details. In other instances, certain structures and devices are shown in block diagram form. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers used herein to express quantities, dimensions, and so forth used should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

One set of embodiments provides rapid, continuous, and/or noninvasive techniques for measuring, estimating, and/or predicting a patient's intracranial pressure. In an aspect, certain embodiments can predict the onset of conditions such as herniation and/or can recommend (and, in some cases, administer) a therapeutic treatment for the patient's condition. In another aspect, some embodiments employ high speed software technology that enables active, long term learning from extremely large, continually changing datasets. In some cases, this technology utilizes feature extraction, state-of-the-art machine learning and/or statistical methods to autonomously build and apply relevant models in real-time.

As noted in the '119 Application, a predictive model can be used not only for medical/physiological data, but also for a wide variety of data sets, including without limitation robotics data, weather data, financial market data, traffic pattern data, etc. More pertinently, however, disclosed embodiments can use a predictive model, as described above, for example, to provide for real time prediction of physiological conditions using various physiological data.

For instance, physiological data can be received (e.g., input) from a physiological sensor that is measuring a physiological state of a patient. Physiological feature data can then be derived from the physiological data. For example, a Finometer (physiological sensor) can be used to measure the blood pressure of a patient and provide blood pressure data (physiological data). From the blood pressure data, blood volume data (physiological feature data) can be derived. Various other physiological feature data can be derived from the physiological data. From the physiological feature data, other physiological parameters (e.g., parameters not amenable to rapid, noninvasive, direct measurement) can be estimated/predicted, and/or a prediction can be made about a physiological threshold where patient state is reached (e.g., trauma or shock). The prediction can be based on a large data set of physiological feature data. Moreover, the prediction can use any type of predictive algorithm and/or can be self learning. In some embodiments, a user interface can provide the physiological feature data along with the predicted threshold. Such a user interface can allow a user to determine whether the physiological feature data is converging and/or diverging with the threshold data.

ICP Model

In particular, certain embodiments employ an experimentally-developed model to correlate estimated and/or predicted ICP with other measured physiological parameters. For example, one such model has been developed using porcine data, collected using an invasive arterial catheter (to collect arterial blood pressure waveform data) and an invasive ICP monitor (to collect ICP data), as well as additional sensors to measure other physiological parameters.

Pursuant to the porcine experiment, twelve pigs were instrumented. An intracranial pressure catheter was placed through a bun hole into the subdural space overlying the animal's right hemisphere. A 12 F catheter-tipped balloon was advanced through a burr hole into the epidural space overlying each animal's left hemisphere. The animals were instrumented with a number of additional catheters to measure cardiac output, stroke volume, aortic pressure, atrial pressure, carotid blood flow ("CBF") and intrathoracic pressure. Once each animal preparation was completed, the left epidural balloon was inflated with 3 ml of saline at a rate of 3 ml/hour until a target ICP of 40 mmHg was achieved. This elevated ICP was due to the increased volume of the inflated balloon. Hemodynamic parameters were continuously measured and blood gases were obtained at the end of the first four 5-minute intervals. Once balloon inflation was complete and a minimum doubling of intracranial pressures was observed, the animals were allowed to stabilize for an additional 30 minutes. The animals were subsequently sacrificed with a potassium bolus and their brains examined for evidence of injury.

The model was developed by processing the porcine data with an algorithm described in further detail below and in the '119 Application to correlate the measured ICP data with the other physiological parameters. ICP predictions were made using a model constructed from data from eleven pigs and tested on the remaining pig. This process was repeated twelve times, with each pig acting as a test pig. The window size used for making predictions was 200 heart beats. The mean correlation coefficient, of all twelve tests, between the ICP measured by the reference sensors and the ICP value estimated by the model (based on aortic waveform data) was 0.92. According to another model, the correlation coefficient between the measured ICP and the ICP value estimated by the model (based on transcranial Doppler waveform data) was 0.90.

Other models, which can be equally valid, can rely on noninvasive blood pressure data and/or can employ human subjects (including without limitation patients themselves). Moreover, a variety of other physiological parameters and/or sensors can be used to develop models and/or to estimate/predict ICP based on those models. Merely by way of example, electrocardiographs ("ECG"), pulse oximeters, volume clamps, impedence cardiographs ("ICG"), near infrared ("NIR") sensors, transcranial Doppler sensors, capnograms, and the like.

The electrocardiograph ("ECG") measures the heart's electrical activity using specifically placed electrodes. The output describes muscle activity through voltages along different directions between electrode pairs. The typical ECG waveform is described as a P wave, a QRS complex, and a T wave. Obviously heart rate ("HR") data can be extracted from the waveform, and considerable attention has been given to heart rate variability ("HRV") for evaluating autonomic dysfunction, and its correlation to events such as increased intracranial pressure and death due to traumatic injury. Some scholars have found that the performance of HRV for predicting traumatic head injury was improved by considering factors such as heart rate, blood pressure, sedation, age, and gender. There are various algorithmic definitions for computing HRV from R-R intervals, which appear to perform equivalently as long as they are calculated over extended (5 min) intervals. ECG poses some challenges for usability in transport as the motion of subjects can alter readings or dislodge sensors.

In their basic form, pulse oximeters use the differing properties of deoxygenated and oxygenated hemoglobin for absorbing red and infrared light. Red ("R") and infrared ("IR") LEDs shine through a relatively translucent site such as the earlobe or finger, and a photodetector on the other side receives the light that passes through. The observed values are used to compute the ratio R/IR, which can be used to look up the patient's saturation of peripheral oxygen ($SpO_2$) level from pre-computed tables. As the heart beats, blood pulses through the arteries in the measurement location causing more light to be absorbed, yielding a waveform of light signals over time. This photoplethysmograph ("PPG") can be used to determine heart rate, but also analyzed in its own right. Subtracting the trough (DC) values, which represent constant light absorbers, we are left with the absorption properties for the varying (AC) component, which is arterial blood.

Advances in technology have seen more 30 light wavelengths used to make systems more reliable by distinguishing $O_2$ and $CO_2$.

Some research recommends the use of the raw PPG signal, and discusses its relationship to systolic blood pressure, sympathetic tone and respiration. PPG has been shown to be correlated to systolic pressure variation ("SPV"), which, in turn, is correlated with hypovolemia. Other researchers compare correlation of ear and finger pulse oximeter waveforms to SBP. They evaluate pulse amplitude, width and area under the curve as extracted features, and use metrics on the envelope of the PPG waveform to reliably detect blood sequestration of more than 1 liter induced by lower body negative pressure ("LBNP"). Still others have constructed a linear predictor for cardiac output ("CO"), based on heart rate and features extracted from the ear PPG waveform.

The Perfusion Index ("PI") expresses the varying versus stationary components of IR light in the PPG as a percentage:

$$PI = \frac{AC_{IR}}{DC_{IR}} \times 100\% \qquad (Eq. 1)$$

Research has established the correlation of PI and core-to-toe temperature difference (a measure of peripheral perfusion) for critically ill patients.

The Pleth Variability Index ("PVI") describes changes in PI over at least one respiratory cycle:

$$PVI = \frac{PI_{max} - PI_{min}}{PI_{max}} \times 100\% \qquad (Eq. 2)$$

It has been shown that PVI can predict fluid responsiveness in anesthetized and ventilated patients. Moreover, PPG variation, pulse pressure variation ("PPV"), and systolic pressure variation ("SPV") are well correlated to gradual autodonation to a reduction of 20% in systolic blood pressure.

The Finopres system used for the USAISR dataset uses a volume clamp mechanism to measure the finger arterial pressure waveform, as well as estimating parameters such as CO, and stroke volume ("SV"). The mechanism combines an infrared plethysmograph to determine baseline unloaded artery diameter and monitor blood volume, and an inflatable finger cuff which is controlled to maintain baseline diameter. Variation in cuff pressure provides an indirect means of measuring intra-arterial pressure.

Similar parameters can be obtained using ICG, which measures volumetric changes due to the cardiac cycle by observing changes in thoracic impedance. Current is passed through the chest between sensors, traveling through the aorta as the path of least resistance. As blood velocity and volume change in the aorta, corresponding changes in impedance are recorded as a continuous waveform, from which hemodynamic parameters such as CO and SV can be computed.

Many standard hemodynamic parameters intended to capture the behavior of the cardiac cycle are derived from blood pressure and heart rate measurements. For example, arterial blood pressure ("ABP") is the pressure in the arteries, which varies through the systolic and diastolic phases of the cardiac cycle. Systolic blood pressure ("SBP") is the maximum ABP as the left ventricle contracts. It can be extracted as the peak values of the raw Finopres ABP waveform. Diastolic blood pressure (DBP) is the ABP when the heart is at rest. It can be measured from the troughs of the APB waveform. Mean arterial pressure ("MAP") describes the mean arterial blood pressure over a cardiac cycle, and it can be expressed as $$MAP = (CO \times SVR) + CVP \qquad (Eq. 3)$$

where CO is cardiac output, SVR is systemic vascular resistance and CVP is central venous pressure. MAP can be approximated using more accessible parameters as:

$$MAP \cong DPB + \frac{1}{2}(SBP - DBP) \qquad (Eq. 4)$$

Systolic pressure variability ("SPV") attempts to measure the change or variability in SBP over a respiration cycle. In general, it is expressed as the difference (or percentage change) between min and max SBP:

$$SPV = SBP_{maxR} - SBP_{minR} \qquad (Eq. 5)$$

Authors will also frequently distinguish delta up ("dUp") and delta down ("dDown") components. Researchers have examined the correlation between SPV and dDown for hemorrhage and volume replacement, finding that they followed intravascular volume for mechanically ventilated patients. Others have concluded that dDown was an effective indicator of CO response to volume replacement for mechanically ventilated septic shock patients. One researcher points out that SPV and dDown should be calculated as percentages of SBP in the case of hypotension.

Pulse pressure (PP) is the beat to beat change in blood pressure:

$$PP = SBP - DBP \qquad (Eq. 6)$$

Pulse pressure variability (PPV) is also computed using min and max PP over the respiratory cycle:

$$PPV = PP_{maxR} - PP_{minR} \qquad (Eq. 7)$$

It has been shown that higher PPV percentages indicated which patients in septic shock responded to fluids and also demonstrated a correlation between PPV and cardiac index. Others have concluded that PPV can be an effective measure for fluid management.

Stroke volume ("SV"), or volume of blood pumped by the left ventricle in a single contraction, is the difference between the volume of blood in the ventricle at the end of the diastolic phase minus the volume of blood remaining after the heart beat:

$$SV = end\_diastolic\_volume - end\_systolic\_volume \qquad (Eq. 8)$$

Since these constituent parameters are difficult to measure, SV is generally estimated from the ABP waveform, and it has been shown that SV and PP derived from finometer BP estimates are correlated with blood loss.

Cardiac Output ("CO") is the volume of blood pumped per unit time:

$$CO = SV \times HR \qquad (Eq. 9)$$

Cardiac index ("CI") relates the performance of the hard to the size of the patient using body surface area ("BSA"):

$$CI = \frac{CO}{BSA} \qquad (Eq. 10)$$

BSA can be estimated using height and mass of the individual. It has been found that CI and mixed venous oxygen saturation showed a linear relationship to blood loss.

Near infrared spectroscopy ("NIRS") has been used for measuring tissue oxygenation since the 1970's. NIR light is shone on the body and deeply penetrates skin, fat and other layers, where it is either scattered or absorbed. As with pulse oximeters the differing absorption characteristics of oxyhemoglobin ("$O_2Hb$") and deoxyhemoglobin (HHb) are used to calculate concentrations based on light received by a detector. Other parameters such as pH and hematocrit can also be extracted from the spectra. Research has modified this process to compensate for the interference of skin and fat layers to better measure muscle oxygen saturation ("$SmO_2$"), and NIRS measurements of $SmO_2$ and pH have been tested as indicators of hemodynamic instability with subjects undergoing LBNP and conclude that 15 $SmO_2$ is an early indicator of vasoconstriction and impending hemodynamic decompensation. Others have compared NIRS forearm measurements of $SmO_2$ and muscle oxygen tension ("$PmO_2$") to $StO_2$ measured at the thenar eminence with a commercial device. They conclude that spectroscopic observations of $PmO_2$ and $SmO_2$ were early indicators of hemodynamic decompensation due to LBNP, while thenar $StO_2$ did not change throughout the test.

Other noninvasive sensors, although less well investigated for the problem of monitoring hemorrhage, offer different system measurements which may contribute a new view to the techniques described herein. Transcranial Doppler uses sound waves (a pulsed Doppler probe) to measure blood flow velocities in cerebral blood vessels (cerebral blood flow CBF velocity). It poses challenges in determining recording locations with a clear path to the vessels of interest, but some have used CBF velocities as an indicator for dynamic cerebral autoregulation under hypervolemia with hemodilution.

The respiration cycle is intimately related to the cardiac cycle and may offer relevant measurements for the problem. A capnogram measures the concentration of $CO_2$ in respiratory gases and is an indirect measure of the $CO_2$ in arterial blood. Infrared light is passed through the gas sample, where $CO_2$ absorbs it and a detector on the other side observes this decrease in light. End tidal $CO_2$ ("$EtCO_2$"), or the $CO_2$ concentration at the end of exhalation, has been determined to have a logarithmic relationship to cardiac output and has been found to track SV in an LBNP model for progressive central hypovolemia, but that the decreases were small relative to baseline measurements for subjects, and concluded that sensors providing continuous trending were required. Other features extracted from sensors include the nonlinear entropy-based features for biosignal analysis.

Any of the above sensors and/or physiological parameters (and/or combinations thereof) can be used to generate models, and/or predict/estimate ICP based on those models, in accordance with various embodiments.

Diagnostic and Therapeutic Techniques

Using an ICP model, various embodiments can estimate a patient's current ICP, predict a patient's future ICP, predict the onset of significant events (such as uncal herniation), recommend therapeutic strategies, and/or implement recommended strategies.

A general overview of a structure used in embodiments of the invention is provided by FIG. 1. The structure includes a computer system 100 in communication with one or more sensors 105, which are configured to obtain physiological data from the subject (e.g., animal or human test subject or patient) 110. An example of a computer system 100 that can be used in some embodiments is described in further detail below. In general, however, the computer system 100 can be any system of one or more computers that are capable of performing the techniques described herein. In a particular embodiment, for example, the computer system 100 is capable of reading values from the physiological sensors 105, generating ICP models from data and/or using the ICP models to make individual-specific predictions, estimates or other diagnoses, displaying the results of the diagnoses, recommending and/or implementing a therapeutic treatment as a result of the analysis, and/or archiving (learning) these results for use in future, model building and predictions The sensors 105 can be any of a variety of sensors (including without limitation those described above) for obtaining physiological data from the subject. By way of example, in an embodiment one or more sensors 105 might obtain, e.g., using one or more of the techniques described above, continuous physiological waveform data, such as SBP, DBP, and/or MAP. Input from the sensors 105 can constitute continuous data signals and/or outcomes that can be used to generate, and/or can be applied to, a predictive model described as described below.

In some cases, the structure might include a therapeutic device 115, which can be controlled by the computer system 100 to administer therapeutic treatment, in accordance with the recommendations developed by analysis of a patient's physiological data. Examples of therapeutic devices can include intravenous pumps, ventilators, anesthesia machines, integrated critical care systems, medical robots, auto-infusers that can provide fluids and/or therapeutic compounds (e.g., through intravenous injection), and/or the like.

FIGS. 2-5 illustrate methods in accordance with various embodiments. While the methods of FIGS. 2-5 are illustrated, for ease of description, as different methods, it should be appreciated that the various techniques and procedures of these methods can be combined in any suitable fashion, and that, in some embodiments, the methods depicted by FIGS. 2-5 can be considered interoperable and/or as portions of a single method. Similarly, while the techniques and procedures are depicted and/or described in a certain order for purposes of illustration, it should be appreciated that certain procedures may be reordered and/or omitted within the scope of various embodiments. Moreover, while the methods illustrated by FIGS. 2-5 can be implemented by (and, in some cases, are described below with respect to) the computer system 100 of FIG. 1 (or components thereof), these methods may also be implemented using any suitable hardware implementation. Similarly, while the computer system 100 of FIG. 1 (and/or components thereof) can operate according to the methods illustrated by FIGS. 2-5 (e.g., by executing instructions embodied on a computer readable medium), the system 100 can also operate according to other modes of operation and/or perform other suitable procedures.

Figure 2:
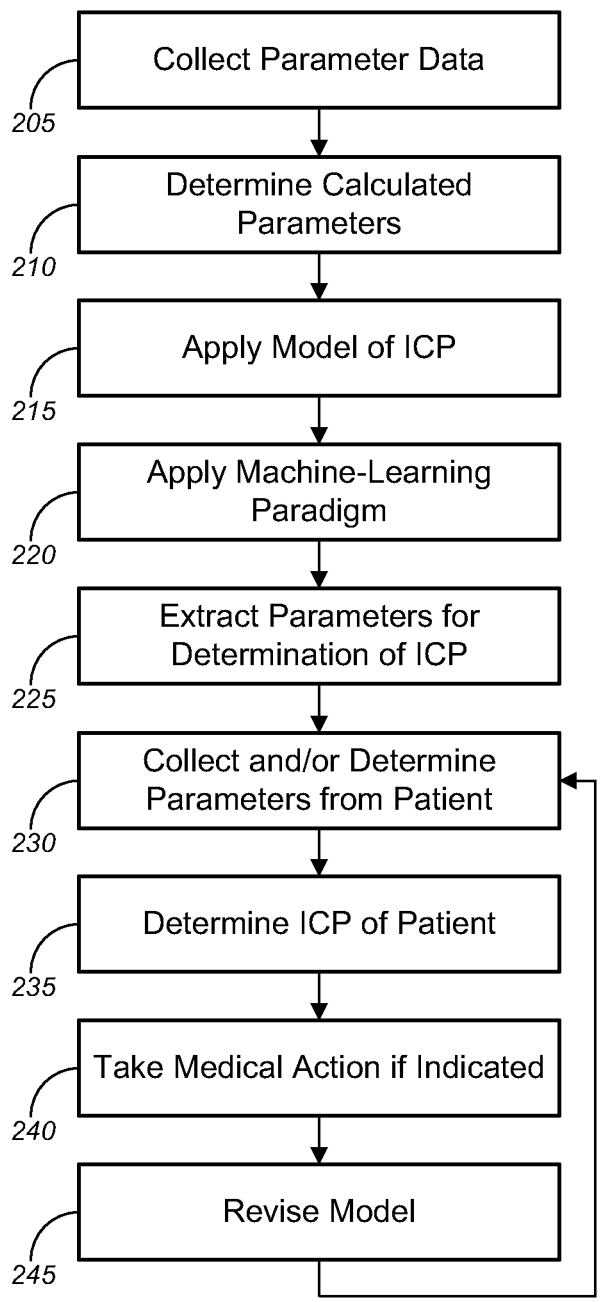
FIG. 2 is a process flow diagram illustrating, in general, a method of measuring ICP noninvasively.

For example, FIG. 2 generally illustrates a method 200 for measuring ICP noninvasively. According to this method 200, physiological parameter data are initially collected from a set of subjects at block 205 and may include both parameters that are collected noninvasively and those that are collected invasively. Examples of noninvasively collected parameters can include continuous noninvasive blood pressure, heart rate, pulse oximetry, transcranial Doppler data, among other potential parameters; examples of invasively collected parameters can continuous blood pressure, central venous pressure, and intracranial pressure, among others (e.g., those described above). As indicated at block 210, some parameters may be calculated, such as mean arterial pressure, cardiac output, and total peripheral resistance, among others.

In addition to these parameters, the intracranial pressure and/or the cerebral perfusion pressure may be measured and calculated so that a model of intracranial pressure may be applied at block 215 to relate such values with the various parameters obtained at blocks 205 and 210. A machine-learning paradigm (e.g., the predictive model described above) can be applied at block 220 to enable the extraction of those parameters that are most relevant to determining the intracranial pressure and/or the cerebral perfusion pressure; the model may then be tailored for prediction of those quantities at block 225.

The resultant model may then be used diagnostically. For instance, the relevant parameters determined at block 225 may be collected at block 230 for a patient presented for diagnosis and the intracranial pressure and/or the cerebral perfusion pressure determined at block 235 by application of the model. If the determined pressure is outside of an acceptable range, medical action may be taken at block 240. In some embodiments, it can be possible for revisions to the model to be made at block 245, particularly after treatment of the patient, in order to improve the value and application of the model.

Evaluation of the model may be made in any of several different ways. For example, a mean square difference of the intracranial pressure predicted by the model and the true estimated intracranial pressure may be calculated. Similarly, mean square difference between the predicted cerebral perfusion pressure and the true estimated cerebral perfusion pressure may be calculated. When a change in intracranial pressure is detected, the time taken for the model to respond to this change in the predicted intracranial pressure or to the predicted cerebral perfusion pressure may be relevant in evaluating the model. In addition, detection of a change in intracranial pressure may be used to calculate the time taken for carotid artery blood flow to diminish and to compare this with the time taken for the model to respond to such a change.

Various studies testing embodiments of the method have enabled the prediction of ICP using hemodynamic measures such as heart rate variability and central hemodynamic pressure. The ability to predict ICP directly from these central hemodynamic parameters stems from the experimentally proven ability to predict blood volume loss and CV collapse onset, using only cranial measures of blood flow derived from intracranial Doppler signals.

Management of traumatic brain injury may include therapies and diagnostic techniques that optimize and monitor cerebral metabolism and function by minimizing global cerebral ischemia. Such therapies may be included in algorithm modifications to allow noninvasive tracking of cerebral pressures.

The machine-learning paradigm accordingly permits the establishment of models that relate such parameters as described above to the intracranial and cerebral perfusion pressures. In particular, it enables the otherwise invasive intracranial and cerebral perfusion pressures to be determined through measurement of noninvasive parameters.

Figure 3:
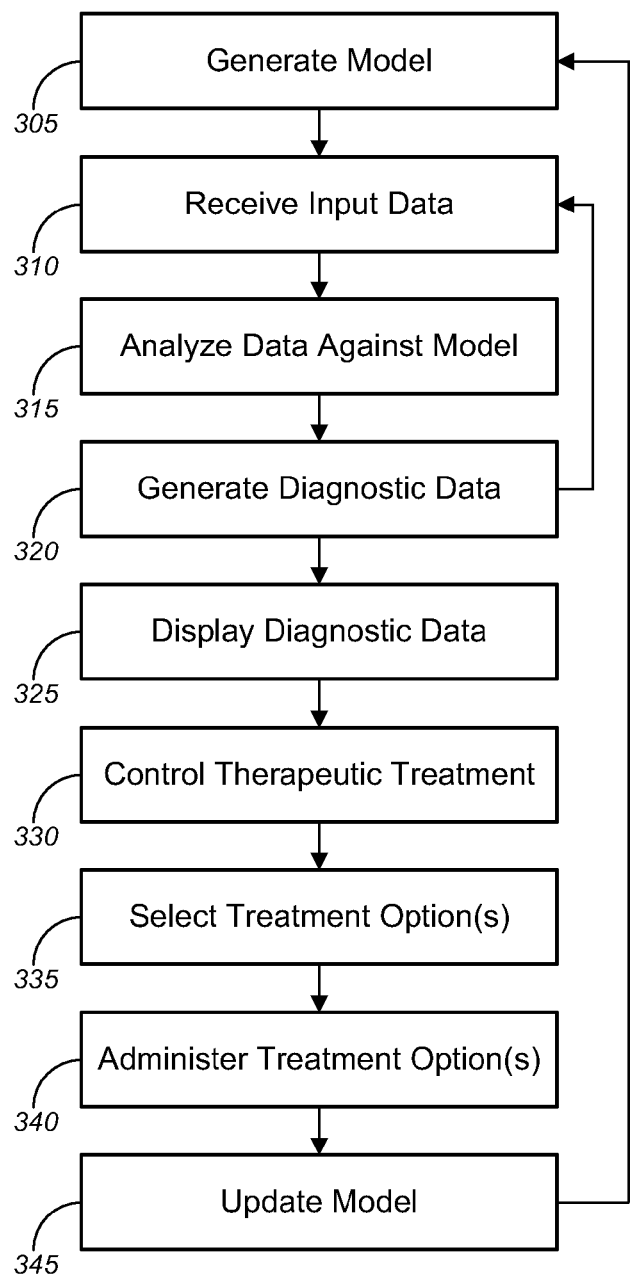
FIG. 3 is a process flow diagram illustrating a method of measuring, estimating, predicting, and/or treating ICP, in accordance with various embodiments.

FIG. 3 illustrates another method 300 of determining the ICP of a patient. The method 300 comprises, at block 305, generating an ICP model, e.g., with a computer system. There are a variety of techniques for generating a model in accordance with different embodiments, some of which are described in further detail above. Another exemplary technique for generating an ICP model is described below with respect to FIG. 4. Any suitable technique or model may be employed in accordance with various embodiments.

At block 310, the method 300 comprises receiving (e.g., at a computer system), a set of input data. In most cases, this input data is obtained by one or more physiological sensors, and the input data pertains to one or more physiological parameters of the patient (which can include, without limitation, some or all of the parameters described above). In an aspect, the sensors may be noninvasive sensors (although invasive sensors can be used as well), and might include, without limitation, electrocardiograph sensors, impedance cardiograph sensors, pulse oximeters, near infrared sensors, continuous noninvasive blood pressure sensors, transcranial Doppler sensors, and/or the like. Such sensors can obtain data about a variety of physiological conditions of the patient, including without limitation, continuous physiological waveform data, such as blood pressure waveform data. The sensors, then, can provide the received data to the computer system, e.g., through standard communication facilities, such as USB, Bluetooth, and/or the like.

At block 315, the input data is analyzed against an ICP model. In some cases, the model is pre-existing (i.e., generated prior to receiving the input data), although, as noted above, the model can be refined using the input data and the results of the analysis itself. In an exemplary case, the model provides an algorithm to which the input data can be applied, to produce output data relating to an estimated/predicted ICP of the patient that corresponds to the patient's measured physiological parameters.

Thus, the analysis of the input data against the model can be used to generate diagnostic data concerning the patient's ICP (block 320). For example, in some cases, the diagnostic data might include an estimate of the patient's current ICP, based on the measured physiological parameters as represented by the data received from the sensors. In other cases, the diagnostic data might include a prediction of the patient's ICP at a time in the future (which might merely be a few seconds, several minutes, one or more hours, etc.), based on, for example, trending in the waveform data received by the sensors, which might correlate to trending patterns predicted by the model Alternatively and/or additionally, the diagnostic data might comprise data about a threshold condition (e.g., ICP value) at which the patient will suffer complications or other conditions. Merely by way of example, in some cases, the model might correlate certain physiological parameter values with the onset of a condition, such as uncal herniation. The model, then, can be used to predict not only future ICP values, but also an ICP value that would likely result in the onset of the condition, based on correlation between the received data about the physiological parameters and the predictions specified by the model.

Figure 6:
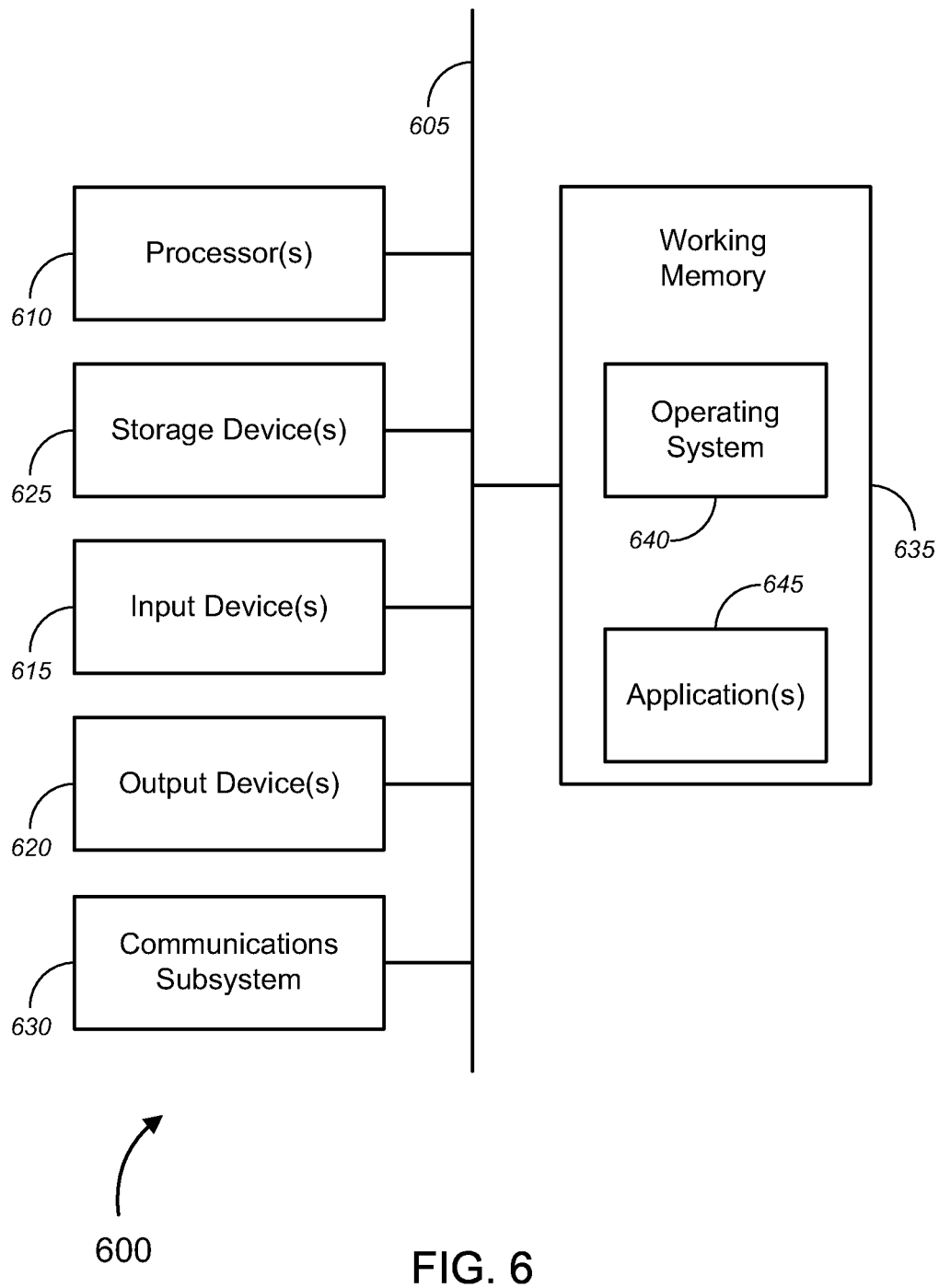
FIG. 6 is a generalized schematic diagram illustrating a computer system, in accordance with various embodiments.

At block 325, the method 300 comprises displaying (e.g., with a display device, such as a computer monitor, a device integrated with a monitoring system, etc.) at least a portion of the diagnostic data. Many different types of displays are possible, including without limitation, textual displays of data, graphical displays (e.g., using one or more graphically-rendered gauges, such as horizontal or vertical bars to illustrate current estimated ICP, predicted ICP, herniation thresholds, etc.), and/or the like. In some cases, displaying the diagnostic data might comprise displaying a tracing of estimated and/or predicted ICP values over time, and/or a predicted time/ICP value that might result in the onset of a condition, such as uncal herniation. Examples of similar tracings, with respect to different physiological parameters and conditions, are illustrated by FIGS. 6 and 11 of the '119 Application. In various embodiments, the system might display ICP diagnostic data, data about other monitored parameters (e.g., data obtained directly by the sensors), and/or both.

At block 330, the method 300 comprises controlling a therapeutic treatment of the patient's ICP, based at least in part on the diagnostic data. More specifically, in some cases the computer system has the ability to participate not only in the diagnosis of a condition (such as elevated ICP) but also in the treatment of that condition, based (in some cases) upon the results of the system's analysis of the measured physiological parameters against the model. Controlling a therapeutic treatment can include many different operations, according to the functionality of the particular embodiment and/or the preferences of the operator.

Merely by way of example, controlling a therapeutic treatment might comprise selecting one or more treatment options from among a plurality of possible treatment options (block 335). For instance, clinical experience has revealed that ICP can be treated in one (or more) of several different fashions. In some cases, administration of a diuretic (such as manitol or the like) can be beneficial at reducing ICP. In other cases, administration of a hyperosmolar solution (such as hypertonic saline or the like) can be beneficial. However, depending on the patient's condition, administration of the wrong therapeutic agent can exacerbate the condition and/or cause other complications. Apparent symptoms of ICP however, often fail to provide any indication to recommend one course of treatment over another. By applying the data about the patient's physiological parameters to the model, however, some embodiments can provide a more sophisticated diagnosis that will indicate which of a plurality of treatment options are preferable. Such embodiments can automatically select a recommended treatment option out of the plurality of treatment options. In an aspect, the system might then display the recommended treatment option on the display device.

Alternatively and/or additionally, controlling a therapeutic treatment might comprise administering the recommended treatment option(s) (block 340). Merely by way of example, as noted above, the system might comprise one or more therapeutic devices, such as intravenous pumps, ventilators, anesthesia machines, integrated critical care systems, medical robots, auto-infusers that can provide fluids and/or therapeutic compounds (e.g., through intravenous injection), and/or the like, and the system might control such a therapeutic device to administer the recommended course of treatment, either automatically and/or based on operator input (e.g., confirmation of a recommended treatment option, etc.).

In some cases, the operations of receiving the input data and analyzing the input data can be repeated, as illustrated by FIG. 3. Thus, for example, a patient can be monitored continuously, with new data being obtained by the sensors, provided to the computer, and applied to the model. The method, then can comprise receiving a plurality of sets of input data, analyzing that data to produce multiple sets of diagnostic data, and providing an updated (e.g., continuously or periodically updated) display of the diagnostic data.

In other cases, the method 300 might comprise updating the ICP model based, at least in part, on the input data and/or the analysis of that data (block 345). Merely by way of example, in some cases, collected data might be used to refine the model. In other cases, if the monitored parameters produce ambiguity when applied to the model, the system might collect data (e.g., from additional sensors) on additional parameters to resolve the ambiguities.

Figure 4:
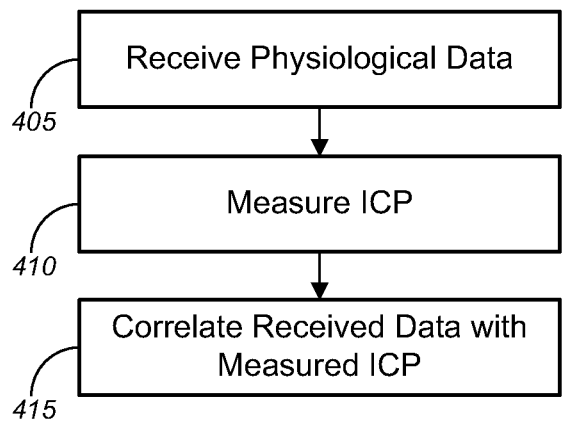
FIG. 4 is a process flow diagram illustrating a method of generating an ICP model.

FIG. 4 illustrates a method of generating an ICP model, which can be used, for example, to analyze input data as described with respect to FIG. 3. The method 400 comprises, at block 405, receiving a plurality of physiological data sets (e.g., obtaining data, such as waveform data, from a plurality of physiological sensors monitoring a test subject). The process of obtaining and/or receiving physiological data sets can be similar to that described above. At block 410, the method 400 comprises directly measuring the test subject's ICP with a reference sensor, to obtain a plurality of ICP measurements. For example, as noted above, the test subject may be instrumented as described above.

At block 415, the method 400 comprises correlating the received data with the measured ICP of the test subject. It is often the case that the correlation between ICP and a given set of one or more physiological parameter is non-trivial. Merely by way of example, relationships between ICP and one or more physiological parameters may be complex and non-linear. Moreover, some combination of different physiological parameters (each having their own coefficient and/or polynomial order) might be most predictive of a condition (such as ICP) in various circumstances.

Accordingly, certain embodiments employ advanced computational techniques, such as those described in the '119 Application, to identify this correlation. Merely by way of example, a particular embodiment employs a self-learning predictive model to identify correlation between ICP and other measured physiological parameters.

Figure 5:
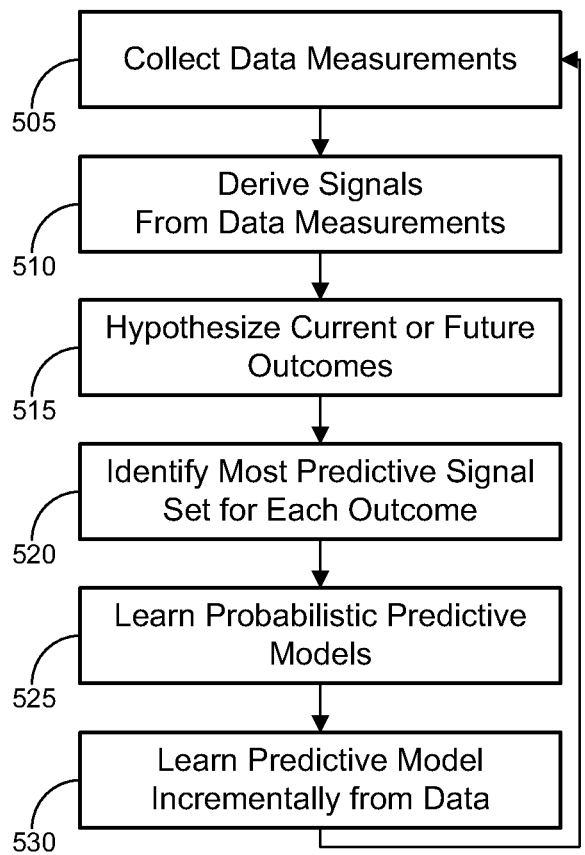
FIG. 5 is a process flow diagram illustrating a method of correlating physiological data with measured ICP of a test subject.

FIG. 5 illustrates a method of employing such a self-learning predictive model (or machine learning) method 500, according to some embodiments. In particular, the method 500 can be used to correlate physiological data received from a subject sensor with measured ICP values. The method 500 begins at block 505 by collecting raw data measurements that may be used to derive a set of D data signals $s_1, \ldots, s_D$ as indicated at block 510 (each of the data signals s being, in a particular case, input from one or many different physiological sensors). Embodiments are not constrained by the type of measurements that are made at block 505 and may generally operate on any data set. For example, data signals can be retrieved from a computer memory and/or can be provided from a sensor or other input device. A set of K current or future outcomes $\vec{o} = (o_1, \ldots, o_K)$ is hypothesized at block 515 (the outcomes o being, in this case, past and/or future measured ICP values). The method autonomously generates a predictive model M that relates the derived data signals $\vec{s}$ with the outcomes $\vec{o}$. As used herein, "autonomous," means "without human intervention."

As indicated at block 520, this is achieved by identifying the most predictive set of signals $S_k$, where $S_k$ contains at least some (and perhaps all) of the derived signals $s_1, \ldots, s_D$ for each outcome $o_k$, where $k \in \{1, \ldots, K\}$. A probabilistic predictive model $\hat{o}_k = M_k(S_k)$ is learned at block 525, where $\hat{o}_k$ is the prediction of outcome $o_k$ derived from the model $M_k$ that uses as inputs values obtained from the set of signals $S_k$, for all $k \in \{1, \ldots, K\}$. The method 500 can learn the predictive models $\hat{o}_k = M_k(S_k)$ incrementally (block 530) from data that contains example values of signals $s_1, \ldots, s_D$ and the corresponding outcomes $o_1, \ldots, o_K$. As the data become available, the method 500 loops so that the data are added incrementally to the model for the same or different sets of signals $S_k$, for all $k \in \{1, \ldots, K\}$.

While the description above outlines the general characteristics of the methods, additional features are noted. A linear model framework may be used to identify predictive variables for each new increment of data. In a specific embodiment, given a finite set of data of signals and outcomes $\{(\vec{s}_1, \vec{o}_1), (\vec{s}_2, \vec{o}_2), \ldots\}$, a linear model may be constructed that has the form, for all $k \in \{1, \ldots, K\}$, $$\hat{o}_k = f_k\left(a_0 + \sum_{i=1}^{d} a_i s_i\right) \quad \text{(Eq. 11)}$$

where $f_k$ is any mapping from one input to one output, and $a_0$, $a_1, \ldots, a_d$ are the linear model coefficients. The framework used to derive the linear model coefficients may estimate which signals $s, s_1, \ldots, s_d$ are not predictive and accordingly sets the corresponding coefficients $a_0, a_1, \ldots, a_d$ to zero. Using only the predictive variables, the model builds a predictive density model of the data, $\{(\vec{s}_1, \vec{o}_1), (\vec{s}_2, \vec{o}_2), \ldots\}$. For each new increment of data, a new predictive density models can be constructed.

In some embodiments, a prediction system can be implemented that can predict future results from previously analyzed data using a predictive model and/or modify the predictive model when data does not fit the predictive model. In some embodiments, the prediction system can make predictions and/or to adapt the predictive model in real-time. Moreover, in some embodiments, a prediction system can use large data sets not only to create the predictive model, but also predict future results as well as adapt the predictive model.

In some embodiments, a self-learning, prediction device can include a data input, a processor and an output. Memory can include application software that when executed can direct the processor to make a prediction from input data based on a predictive model. Any type of predictive model can be used that operates on any type of data. In some embodiments, the predictive model can be implemented for a specific type of data. In some embodiments, when data is received the predictive model can determine whether it understands the data according to the predictive model. If the data is understood, a prediction is made and the appropriate output provided based on the predictive model. If the data is not understood when received, then the data can be added to the predictive model to modify the model. In some embodiments, the device can wait to determine the result of the specified data and can then modify the predictive model accordingly. In some embodiments, if the data is understood by the predictive model and the output generated using the predictive model is not accurate, then the data and the outcome can be used to modify the predictive model. In some embodiments, modification of the predictive model can occur in real-time.

FIG. 6 provides a schematic illustration of one embodiment of a computer system 600 that can perform the methods provided by various other embodiments, as described herein, and/or can function the computer system of FIG. 1, a patient monitoring system, and/or the like. It should be noted that FIG. 6 is meant only to provide a generalized illustration of various components, of which one or more (or none) of each may be utilized as appropriate. FIG. 6, therefore, broadly illustrates how individual system elements may be implemented in a relatively separated or relatively more integrated manner.

The computer system 600 is shown comprising hardware elements that can be electrically coupled via a bus 605 (or may otherwise be in communication, as appropriate). The hardware elements may include one or more processors 610, including without limitation one or more general-purpose processors and/or one or more special-purpose processors (such as digital signal processing chips, graphics acceleration processors, and/or the like); one or more input devices 615, which can include without limitation a mouse, a keyboard and/or the like; and one or more output devices 620, which can include without limitation a display device, a printer and/or the like.

The computer system 600 may further include (and/or be in communication with) one or more storage devices 625, which can comprise, without limitation, local and/or network accessible storage, and/or can include, without limitation, a disk drive, a drive array, an optical storage device, solid-state storage device such as a random access memory ("RAM") and/or a read-only memory ("ROM"), which can be programmable, flash-updateable and/or the like. Such storage devices may be configured to implement any appropriate data stores, including without limitation, various file systems, database structures, and/or the like.

The computer system 600 might also include a communications subsystem 630, which can include without limitation a modem, a network card (wireless or wired), an infra-red communication device, a wireless communication device and/or chipset (such as a Bluetooth™ device, an 802.11 device, a WiFi device, a WiMax device, a WWAN device, cellular communication facilities, etc.), and/or the like. The communications subsystem 630 may permit data to be exchanged with a network (such as the network described below, to name one example), with other computer systems, and/or with any other devices described herein. For example, in various embodiments, the communications subsystem provides connectivity for the computer to control and/or receive data from one or more sensors, and/or to control a therapeutic device, as described above. Alternatively and/or additionally, the sensors and/or the therapeutic device might be integrated with the computer system itself.

In many embodiments, the computer system 600 will further comprise a working memory 635, which can include a RAM or ROM device, as described above. The computer system 600 also may comprise software elements, shown as being currently located within the working memory 635, including an operating system 640, device drivers, executable libraries, and/or other code, such as one or more application programs 645, which may comprise computer programs provided by various embodiments, and/or may be designed to implement methods, and/or configure systems, provided by other embodiments, as described herein. Merely by way of example, one or more procedures described with respect to the method(s) discussed above might be implemented as code and/or instructions executable by a computer (and/or a processor within a computer); in an aspect, then, such code and/or instructions can be used to configure and/or adapt a general purpose computer (or other device) to perform one or more operations in accordance with the described methods.

A set of these instructions and/or code might be encoded and/or stored on a non-transitory computer readable storage medium, such as the storage device(s) 625 described above. In some cases, the storage medium might be incorporated within a computer system, such as the system 600. In other embodiments, the storage medium might be separate from a computer system (i.e., a removable medium, such as a compact disc, etc.), and/or provided in an installation package, such that the storage medium can be used to program, configure and/or adapt a general purpose computer with the instructions/code stored thereon. These instructions might take the form of executable code, which is executable by the computer system 600 and/or might take the form of source and/or installable code, which, upon compilation and/or installation on the computer system 600 (e.g., using any of a variety of generally available compilers, installation programs, compression/decompression utilities, etc.) then takes the form of executable code.

It will be apparent to those skilled in the art that substantial variations may be made in accordance with specific requirements. For example, customized hardware (such as programmable logic controllers, field-programmable gate arrays, application-specific integrated circuits, and/or the like) might also be used, and/or particular elements might be implemented in hardware, software (including portable software, such as applets, etc.), or both. Further, connection to other computing devices such as network input/output devices may be employed.

As mentioned above, in one aspect, some embodiments may employ a computer system (such as the computer system 600) to perform methods in accordance with various embodiments of the invention. According to a set of embodiments, some or all of the procedures of such methods are performed by the computer system 600 in response to processor 610 executing one or more sequences of one or more instructions (which might be incorporated into the operating system 640 and/or other code, such as an application program 645) contained in the working memory 635. Such instructions may be read into the working memory 635 from another computer readable medium, such as one or more of the storage device(s) 625. Merely by way of example, execution of the sequences of instructions contained in the working memory 635 might cause the processor(s) 610 to perform one or more procedures of the methods described herein.

The terms "machine readable medium" and "computer readable medium," as used herein, refer to any medium that participates in providing data that causes a machine to operation in a specific fashion. In an embodiment implemented using the computer system 600, various computer readable media might be involved in providing instructions/code to processor(s) 610 for execution and/or might be used to store and/or carry such instructions/code (e.g., as signals). In many implementations, a computer readable medium is a non-transitory, physical and/or tangible storage medium. Such a medium may take many forms, including but not limited to, non-volatile media, volatile media, and transmission media. Non-volatile media includes, for example, optical and/or magnetic disks, such as the storage device(s) 625. Volatile media includes, without limitation, dynamic memory, such as the working memory 635. Transmission media includes, without limitation, coaxial cables, copper wire and fiber optics, including the wires that comprise the bus 605, as well as the various components of the communication subsystem 630 (and/or the media by which the communications subsystem 630 provides communication with other devices). Hence, transmission media can also take the form of waves (including without limitation radio, acoustic and/or light waves, such as those generated during radio-wave and infrared data communications).

Common forms of physical and/or tangible computer readable media include, for example, a floppy disk, a flexible disk, a hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read instructions and/or code.

Various forms of computer readable media may be involved in carrying one or more sequences of one or more instructions to the processor(s) 610 for execution. Merely by way of example, the instructions may initially be carried on a magnetic disk and/or optical disc of a remote computer. A remote computer might load the instructions into its dynamic memory and send the instructions as signals over a transmission medium to be received and/or executed by the computer system 600. These signals, which might be in the form of electromagnetic signals, acoustic signals, optical signals and/or the like, are all examples of carrier waves on which instructions can be encoded, in accordance with various embodiments of the invention.

The communications subsystem 630 (and/or components thereof) generally will receive the signals, and the bus 605 then might carry the signals (and/or the data, instructions, etc. carried by the signals) to the working memory 635, from which the processor(s) 605 retrieves and executes the instructions. The instructions received by the working memory 635 may optionally be stored on a storage device 625 either before or after execution by the processor(s) 610.

While certain features and aspects have been described with respect to exemplary embodiments, one skilled in the art will recognize that numerous modifications are possible. For example, the methods and processes described herein may be implemented using hardware components, software components, and/or any combination thereof. Further, while various methods and processes described herein may be described with respect to particular structural and/or functional components for ease of description, methods provided by various embodiments are not limited to any particular structural and/or functional architecture but instead can be implemented on any suitable hardware, firmware and/or software configuration. Similarly, while certain functionality is ascribed to certain system components, unless the context dictates otherwise, this functionality can be distributed among various other system components in accordance with the several embodiments.

Moreover, while the procedures of the methods and processes described herein are described in a particular order for ease of description, unless the context dictates otherwise, various procedures may be reordered, added, and/or omitted in accordance with various embodiments. Moreover, the procedures described with respect to one method or process may be incorporated within other described methods or processes; likewise, system components described according to a particular structural architecture and/or with respect to one system may be organized in alternative structural architectures and/or incorporated within other described systems. Hence, while various embodiments are described with—or without—certain features for ease of description and to illustrate exemplary aspects of those embodiments, the various components and/or features described herein with respect to a particular embodiment can be substituted, added and/or subtracted from among other described embodiments, unless the context dictates otherwise. Consequently, although several exemplary embodiments are described above, it will be appreciated that the invention is intended to cover all modifications and equivalents within the scope of the following claims.

What is claimed is:

1. A computational method of predicting intracranial pressure, the method comprising:
   generating a model of intracranial pressure, wherein generating the model comprises:
   receiving data pertaining to a plurality of physiological parameters of a test subject to obtain a plurality of physiological data sets;
   directly measuring the test subject's intracranial pressure with a reference sensor to obtain a plurality of intracranial pressure measurements; and correlating the received data with the measured intracranial pressure of the test subject, wherein correlating the received data with the measured intracranial pressure comprises:
  identifying a most-predictive set of signals $S_k$ out of a set of signals $s_1, s_2, \ldots, s_D$ for each of one or more outcomes $o_k$, wherein the most-predictive set of signals $S_k$ corresponds to a first data set representing a first physiological parameter, and wherein each of the one or more outcomes $o_k$ represents one of the plurality of intracranial pressure measurements;
  autonomously learning a set of probabilistic predictive models $\hat{o}_k = M_k(S_k)$, where $\hat{o}_k$ is a prediction of outcome $o_k$ derived from a model $M_k$ that uses as inputs values obtained from the set of signals $S_k$; and
  repeating the operation of autonomously learning incrementally from data that contains examples of values of signals $s_1, s_2, \ldots, s_D$ and corresponding outcomes $o_1, o_2, \ldots, o_K$;
receiving, at a computer system, a set of input data from one or more physiological sensors, the input data pertaining to one or more physiological parameters of a patient;
analyzing, with the computer system, the input data against the model to generate diagnostic data concerning the patient's intracranial pressure; and
displaying, with a display device, at least a portion of the diagnostic data concerning the patient's intracranial pressure.

2. The method of claim 1, wherein the diagnostic data comprises an estimate of a current intracranial pressure of the patient.

3. The method of claim 1, wherein the diagnostic data comprises an estimated intracranial pressure at which the patient will suffer uncal herniation.

4. The method of claim 1, wherein the diagnostic data comprises one or more predictions of a future intracranial pressure of the patient.

5. The method of claim 1, wherein the method is noninvasive to the patient, and wherein the one or more physiological sensors are noninvasive sensors.

6. The method of claim 1, further comprising:
controlling, with the computer system, a therapeutic treatment of the patient's intracranial pressure, based at least in part on the generated diagnostic data.

7. The method of claim 6, wherein controlling a therapeutic treatment comprises selecting one or more recommended treatment options, out of a plurality of treatment options.

8. The method of claim 7, wherein controlling a therapeutic treatment further comprises administering, with the computer system, the one or more recommended treatment options.

9. The method of claim 7, wherein the plurality of treatment options comprises a first treatment option comprising administration of a hyperosmolar solution and a second treatment option comprising administration of a diuretic agent.

10. The method of claim 1, further comprising:
repeating the operation of receiving a set of input data over a plurality of iterations, to produce a plurality of sets of input data, wherein analyzing the input data comprises analyzing the plurality of sets of input data to generate a plurality of sets of diagnostic data;
wherein displaying at least a portion of the diagnostic data comprises updating a display on the display device to display at least some of the plurality of sets of diagnostic data over the period of time.

11. The method of claim 10, wherein the plurality of sets of input data comprise periodic samples of a set of continuous, physiological waveform data.

12. The method of claim 11, wherein the set of continuous, physiological waveform data comprises blood pressure waveform data.

13. The method of claim 1, wherein the one or more physiological sensors comprise an electrocardiograph sensor.

14. The method of claim 1, wherein the one or more physiological sensors comprise an impedance cardiograph sensor.

15. The method of claim 1, wherein the one or more physiological sensors comprise a pulse oximeter.

16. The method of claim 1, wherein the one or more physiological sensors comprise a near infrared sensor.

17. The method of claim 1, wherein the one or more physiological sensors comprise a transcranial Doppler sensor.

18. The method of claim 1, wherein autonomously learning the set of probabilistic predictive models comprises using a linear model framework to identify predictive variables for each increment of data.

19. The method of claim 18, wherein the linear model framework is constructed with the form $$\hat{o}_k = f_k\left(a_0 + \sum_{i=1}^{d} a_i s_i\right),$$

where $f_k$ is any mapping from one input to one output and $a_0, a_1, \ldots, a_d$ are linear model coefficients.

20. The method of claim 1, further comprising:
updating the model using the set of input data.

21. An apparatus, comprising:
a non-transitory computer readable medium having encoded thereon a set of instructions executable by one or more computers to perform one or more operations, the set of instructions comprising:
  instructions for generating a model of intracranial pressure, wherein the instructions for generating the model comprise:
    instructions for receiving data pertaining to a plurality of physiological parameters of a test subject to obtain a plurality of physiological data sets;
    instructions for directly measuring the test subject's intracranial pressure with a reference sensor to obtain a plurality of intracranial pressure measurements; and
    instructions for correlating the received data with the measured intracranial pressure of the test subject, wherein the instructions for correlating the received data with the measured intracranial pressure comprise:
      instructions for identifying a most-predictive set of signals $S_k$ out of a set of signals $s_1, s_2, \ldots, s_D$ for each of one or more outcomes $o_k$, wherein the most-predictive set of signals $S_k$ corresponds to a first data set representing a first physiological parameter, and wherein each of the one or more outcomes $o_k$ represents one of the plurality of intracranial pressure measurements;
      instructions for autonomously learning a set of probabilistic predictive models $\hat{o}_k = M_k(S_k)$, where $\hat{o}_k$ is a prediction of outcome $o_k$ derived from a model $M_k$ that uses as inputs values obtained from the set of signals $S_k$; and
      instructions for repeating the operation of autonomously learning incrementally from data that contains examples of values of signals $s_1, s_2, \ldots, s_D$ and corresponding outcomes $o_1, o_2, \ldots, o_K$;

instructions for receiving a set of input data from one or more physiological sensors, the input pertaining to one or more physiological parameters of a patient;

instructions for analyzing the input data against the model to generate diagnostic data concerning the patient's intracranial pressure; and instructions for displaying, with a display device, at least a portion of the diagnostic data concerning the patient's intracranial pressure.

22. A system, comprising:

a computer system, comprising:

one or more processors; and a computer readable medium in communication with the one or more processors, the computer readable medium having encoded thereon a set of instructions executable by the computer system to perform one or more operations, the set of instructions comprising:

instructions for generating a model of intracranial pressure, wherein the instructions for generating the model comprise:

instructions for receiving data pertaining to a plurality of physiological parameters of a test subject to obtain a plurality of physiological data sets;

instructions for directly measuring the test subject's intracranial pressure with a reference sensor to obtain a plurality of intracranial pressure measurements; and instructions for correlating the received data with the measured intracranial pressure of the test subject, wherein the instructions for correlating the received data with the measured intracranial pressure comprise:

instructions for identifying a most-predictive set of signals $S_k$ out of a set of signals $s_1, s_2, \ldots, s_D$ for each of one or more outcomes $o_k$, wherein the most-predictive set of signals $S_k$ corresponds to a first data set representing a first physiological parameter, and wherein each of the one or more outcomes $o_K$ represents one of the plurality of intracranial pressure measurements;

instructions for autonomously learning a set of probabilistic predictive models $\hat{o}_k = M_k(S_k)$, where $\hat{o}_k$ is a prediction of outcome $o_k$ derived from a model $M_k$ that uses as inputs values obtained from the set of signals $S_k$; and instructions for repeating the operation of autonomously learning incrementally from data that contains examples of values of signals $s_1, s_2, \ldots, s_D$ and corresponding outcomes $o_1, o_2, \ldots, o_K$;

instructions for receiving a set of input data from one or more physiological sensors, the input pertaining to one or more physiological parameters of a patient;

instructions for analyzing the input data against the model to generate diagnostic data concerning the patient's intracranial pressure; and instructions for displaying, with a display device, at least a portion of the diagnostic data concerning the patient's intracranial pressure.

23. The system of claim 22, further comprising the one or more physiological sensors.

24. The apparatus of claim 21, wherein the diagnostic data comprises an estimate of a current intracranial pressure of the patient.

25. The apparatus of claim 21, wherein the diagnostic data comprises an estimated intracranial pressure at which the patient will suffer uncal herniation.

26. The apparatus of claim 21, wherein the diagnostic data comprises one or more predictions of a future intracranial pressure of the patient.

27. The apparatus of claim 21, wherein the input data is received by a technique that is noninvasive to the patient, and wherein the one or more physiological sensors are noninvasive sensors.

28. The apparatus of claim 21, the set of instructions further comprising:

instructions for controlling a therapeutic treatment of the patient's intracranial pressure, based at least in part on the generated diagnostic data.

29. The apparatus of claim 28, wherein controlling a therapeutic treatment comprises selecting one or more recommended treatment options, out of a plurality of treatment options.

30. The apparatus of claim 29, wherein controlling a therapeutic treatment further comprises administering, with the computer system, the one or more recommended treatment options.

31. The apparatus of claim 30, wherein the plurality of treatment options comprises a first treatment option comprising administration of a hyperosmolar solution and a second treatment option comprising administration of a diuretic agent.

32. The apparatus of claim 21, the set of instructions further comprising:

instructions for repeating the operation of receiving a set of input data over a plurality of iterations, to produce a plurality of sets of input data, wherein analyzing the input data comprises analyzing the plurality of sets of input data to generate a plurality of sets of diagnostic data;

wherein displaying at least a portion of the diagnostic data comprises updating a display on the display device to display at least some of the plurality of sets of diagnostic data over the period of time.

33. The apparatus of claim 32, wherein the plurality of sets of input data comprise periodic samples of a set of continuous, physiological waveform data.

34. The apparatus of claim 33, wherein the set of continuous, physiological waveform data comprises blood pressure waveform data.

35. The apparatus of claim 21, wherein the one or more physiological sensors comprise an electrocardiograph sensor.

36. The apparatus of claim 21, wherein the one or more physiological sensors comprise an impedance cardiograph sensor.

37. The apparatus of claim 21, wherein the one or more physiological sensors comprise a pulse oximeter.

38. The apparatus of claim 21, wherein the one or more physiological sensors comprise a near infrared sensor.

39. The apparatus of claim 21, wherein the one or more physiological sensors comprise a transcranial Doppler sensor.

40. The apparatus of claim 21, wherein autonomously learning the set of probabilistic predictive models comprises using a linear model framework to identify predictive variables for each increment of data.

41. The apparatus of claim 40, wherein the linear model framework is constructed with the form $$\hat{o}_k = f_k\left(a_0 + \sum_{i=1}^{d} a_i s_i\right),$$

where $f_k$ is any mapping from one input to one output and $a_0, a_1, \ldots, a_d$ are linear model coefficients.

42. The apparatus of claim 21, the set of instructions further comprising:
instructions for updating the model using the set of input data.

43. The system of claim 22, wherein the diagnostic data comprises an estimate of a current intracranial pressure of the patient.

44. The system of claim 22, wherein the diagnostic data comprises an estimated intracranial pressure at which the patient will suffer uncal herniation.

45. The system of claim 22, wherein the diagnostic data comprises one or more predictions of a future intracranial pressure of the patient.

46. The system of claim 22, wherein the input data is received by a technique that is noninvasive to the patient, and wherein the one or more physiological sensors are noninvasive sensors.

47. The system of claim 22, the set of instructions further comprising:
instructions for controlling a therapeutic treatment of the patient's intracranial pressure, based at least in part on the generated diagnostic data.

48. The system of claim 47, wherein controlling a therapeutic treatment comprises selecting one or more recommended treatment options, out of a plurality of treatment options.

49. The system of claim 48, wherein controlling a therapeutic treatment further comprises administering, with the computer system, the one or more recommended treatment options.

50. The system of claim 49, wherein the plurality of treatment options comprises a first treatment option comprising administration of a hyperosmolar solution and a second treatment option comprising administration of a diuretic agent.

51. The system of claim 22, the set of instructions further comprising:
instructions for repeating the operation of receiving a set of input data over a plurality of iterations, to produce a plurality of sets of input data, wherein analyzing the input data comprises analyzing the plurality of sets of input data to generate a plurality of sets of diagnostic data;
wherein displaying at least a portion of the diagnostic data comprises updating a display on the display device to display at least some of the plurality of sets of diagnostic data over the period of time.

52. The system of claim 51, wherein the plurality of sets of input data comprise periodic samples of a set of continuous, physiological waveform data.

53. The system of claim 22, wherein the set of continuous, physiological waveform data comprises blood pressure waveform data.

54. The system of claim 22, wherein the one or more physiological sensors comprise an electrocardiograph sensor.

55. The apparatus of claim 21, wherein the one or more physiological sensors comprise an impedance cardiograph sensor.

56. The system of claim 22, wherein the one or more physiological sensors comprise a pulse oximeter.

57. The system of claim 22, wherein the one or more physiological sensors comprise a near infrared sensor.

58. The system of claim 22, wherein the one or more physiological sensors comprise a transcranial Doppler sensor.

59. The system of claim 22, wherein autonomously learning the set of probabilistic predictive models comprises using a linear model framework to identify predictive variables for each increment of data.

60. The system of claim 59, wherein the linear model framework is $$\hat{o}_k = f_k\left(a_0 + \sum_{i=1}^{d} a_i s_i\right),$$

constructed with the form where $f_k$ is any mapping from one input to one output and $a_0, a_1, \ldots, a_d$ are linear model coefficients.

61. The system of claim 22, the set of instructions further comprising:
instructions for updating the model using the set of input data.

* * * * *

UNITED STATES PATENT AND TRADEMARK OFFICE
CERTIFICATE OF CORRECTION

PATENT NO. : 8,512,260 B2  Page 1 of 1
APPLICATION NO. : 13/028140
DATED : August 20, 2013
INVENTOR(S) : Gregory Zlatko Grudic et al.

It is certified that error appears in the above-identified patent and that said Letters Patent is hereby corrected as shown below:

On the Title Page, Item (75) 3rd Inventor should read -- Isobel Jane Mulligan --.

Signed and Sealed this
Twenty-sixth Day of August, 2014

Michelle K. Lee
*Deputy Director of the United States Patent and Trademark Office*